US012685821B2

(12) United States Patent
Karlsson

(10) Patent No.: US 12,685,821 B2
(45) Date of Patent: Jul. 21, 2026

(54) MEDICAMENT DELIVERY DEVICE

(71) Applicant: SHL MEDICAL AG, Zug (CH)

(72) Inventor: Sebastian Karlsson, Stigtomta (SE)

(73) Assignee: SHL Medical AG, Zug (CH)

( * ) Notice: Subject to any disclaimer, the term of this patent is extended or adjusted under 35 U.S.C. 154(b) by 530 days.

(21) Appl. No.: 18/221,024

(22) Filed: Jul. 12, 2023

(65) Prior Publication Data

US 2023/0347055 A1 Nov. 2, 2023

Related U.S. Application Data

(63) Continuation of application No. 17/775,650, filed as application No. PCT/EP2020/081861 on Nov. 12, 2020.

(Continued)

(30) Foreign Application Priority Data

Dec. 19, 2019 (EP) .................................... 19218017

(51) Int. Cl.
| | |
|---|---|
| *A61M 5/20* | (2006.01) |
| *A61M 5/315* | (2006.01) |
| *A61M 5/32* | (2006.01) |

(52) U.S. Cl.
CPC ...... *A61M 5/2033* (2013.01); *A61M 5/31553* (2013.01); *A61M 5/3272* (2013.01)

(58) Field of Classification Search
CPC ............ A61M 5/2033; A61M 5/31553; A61M 5/3272
See application file for complete search history.

(56) References Cited

U.S. PATENT DOCUMENTS

| | | |
|---|---|---|
| 2005/0203466 A1 | 9/2005 | Hommann |
| 2008/0228147 A1* | 9/2008 | David-Hegerich ... A61M 5/326 604/198 |

(Continued)

FOREIGN PATENT DOCUMENTS

| | | |
|---|---|---|
| CN | 102892446 A | 1/2013 |
| CN | 104684604 A | 6/2015 |

(Continued)

OTHER PUBLICATIONS

International Search Report and Written Opinion for Int. App. No. PCT/EP2020/081861, mailed Nov. 30, 2020.

*Primary Examiner* — Dung T Ulsh
(74) *Attorney, Agent, or Firm* — McDonnell Boehnen Hulbert & Berghoff LLP

(57) ABSTRACT

A medicament delivery device is presented having a housing with a proximal end and a distal end, a medicament container arranged within the housing, a biased delivery member cover associated with the housing and movable in relation to the housing, a biased plunger rod associated with the medicament container and movable in relation to the housing, a tubular rotator associated with both the delivery member cover and the biased plunger rod, and a cap assembly associated with the housing, wherein a gap is defined between the proximal end of the biased plunger rod and the stopper of the medicament container when the medicament delivery device is in an assembled state, and wherein the proximal end of the biased plunger rod is in contact with the stopper of the medicament container when the medicament delivery device is in a calibrated state.

20 Claims, 13 Drawing Sheets

Related U.S. Application Data

(60) Provisional application No. 62/946,454, filed on Dec. 11, 2019.

(56) References Cited

U.S. PATENT DOCUMENTS

| | | | |
|---|---|---|---|
| 2012/0330244 A1 | 12/2012 | Helmer et al. | |
| 2013/0030409 A1 | 1/2013 | Macdonald et al. | |
| 2014/0257185 A1 | 9/2014 | Bechmann | |
| 2016/0287802 A1* | 10/2016 | Blancke | A61M 5/31575 |
| 2016/0331904 A1 | 11/2016 | Huthmacher et al. | |

FOREIGN PATENT DOCUMENTS

| | | | |
|---|---|---|---|
| EP | 2902061 A1 | 8/2015 | |
| JP | 2008-521482 A | 6/2008 | |
| JP | 2008-526455 A | 7/2008 | |
| WO | 2003053499 A1 | 7/2003 | |
| WO | 2005009515 A1 | 2/2005 | |
| WO | 2006/057604 A1 | 6/2006 | |
| WO | 2007131013 A1 | 11/2007 | |
| WO | 2007131025 A1 | 11/2007 | |
| WO | 2009114542 A1 | 9/2009 | |
| WO | 2009137486 A1 | 11/2009 | |
| WO | 2010017650 A1 | 2/2010 | |
| WO | 2010023481 A1 | 3/2010 | |
| WO | 2010149214 A1 | 12/2010 | |
| WO | 2011003980 A1 | 1/2011 | |
| WO | 2011/039219 A2 | 4/2011 | |
| WO | 2011/042538 A1 | 4/2011 | |
| WO | 2011039231 A1 | 4/2011 | |
| WO | 2011048223 A1 | 4/2011 | |
| WO | 2011/113868 A1 | 9/2011 | |
| WO | 2012163890 A1 | 12/2012 | |
| WO | 2013016832 A1 | 2/2013 | |
| WO | 2013/048310 A1 | 4/2013 | |
| WO | 2013092670 A1 | 6/2013 | |
| WO | 2013156516 A1 | 10/2013 | |
| WO | 2013169800 A1 | 11/2013 | |
| WO | 2015074983 A2 | 5/2015 | |
| WO | 2015087090 A2 | 6/2015 | |
| WO | 2015166286 A2 | 11/2015 | |
| WO | WO-2017102175 A1 * | 6/2017 | A61M 5/2033 |
| WO | 2021199034 A1 | 10/2021 | |

* cited by examiner

MEDICAMENT DELIVERY DEVICE

CROSS REFERENCE TO RELATED APPLICATIONS

The present application is a continuation of U.S. patent application Ser. No. 17/775,650, filed May 10, 2022, which is a U.S. National Phase Application pursuant to 35 U.S.C. § 371 of International Application No. PCT/EP2020/081861 filed Nov. 12, 2020, which claims priority to U.S. Provisional Patent Application No. 62/946,454 filed Dec. 11, 2019 and European Patent Application No. 19218017.2, filed Dec. 19, 2019. The entire disclosure contents of these applications are herewith incorporated by reference into the present application.

TECHNICAL FIELD

The present disclosure relates to a medicament delivery device and more particularly to the medicament delivery device with automatic functions.

BACKGROUND

Medicament delivery devices such as auto-injectors, inhalers, on-body devices are generally known for the self-administration of a medicament by patients without formal medical training occurs. For example, those patients suffering from diabetes or those people are taking the artificial fertilization procedure may require repeated injections of insulin or hormone. Other patients may require regular injections of other types of medicaments, such as a growth hormone.

Medicament delivery devices may be delivery to end users with prefilled medicament containers. A medicament container usually constructed by a glass or plastic barrel with a stopper sealing on its rear end and a delivery member arranged on its front end; or a pierceable membrane arranged on its front end. Most of time, the medicament container will be filed with specific medicament first, then be assembled into a medicament delivery device. The medicament delivery device usually comprises a plunger rod configured to push on the stopper of the medicament container to deliver the contained medicament to an end user. However, when the medicament is filing into medicament containers and stoppers are placing to seal medicament containers, the position of stoppers in each medicament container might be different. The difference is caused by multiple factors, such as the manufacture temperature and/or pressure, the spread of silicone oil in medicament containers, the surface tension force of the medicament and/or the delivery member. Even a batch of medicament containers have been perfectly filed with the medicament and position of each stopper are all the same, when the batch is shipping to a market distributer or a medicament delivery device manufacturer through air transport, those positions of each stopper may change due to the pressure difference. Since the difference of the stopper position in each medicament container, a plunger rod in a medicament delivery device usually be arranged rearward and has a gap to the stopper of the assembled medicament container. Otherwise, if the plunger rod is arranged too close to the stopper of the assembled medicament container, there may be a risk that the plunger rod squeezes the stopper during assembling or during shipping by air transport which may result as the damage of the medicament container due to the increased interior pressure or contamination by a leakage of the contained medicament.

However, the length size of the gap dependent on the position of the stopper and may be different in each assembled medicament delivery device, therefore, a risk of dose inaccuracy may be raised. A medicament delivery device required high delivered dose accuracy usually will arranged with an overfilled medicament container and a plunger rod with specific hard stop arrangement. The delivered dose is determined by the travel distance of the plunger rod, not the entire amount of the medicament contained in the medicament. However, with the difference of the length size of the gap between the front end of the plunger rod and the rear end of the stopper of the medicament container, the delivered dose is actually determined by subtracting the length size of the gap from the travel distance of the plunger rod; therefore, the difference of the length size of the gap raises the risk of delivered dose inaccuracy.

The document WO 2006/057604 discloses a medicament delivery device provided with a number of automatic functions, which medicament delivery device has been very well received on the market. The medicament delivery device comprises a rotator and a needle shield with a needle shield link, the axial movement of the needle shield link is configured to run along ledges on the outer surface of the rotator and causes the rotator to rotate. The rotation of the rotator is arranged to release the biased plunger comprising a stop member that resting on the inner ledge of the rotator.

In most instances this solution works very well. However, there is also a demand to have a further improvement on the disclosed medicament delivery device.

SUMMARY

The aim of the present disclosure is to obtain alternative and more robust solutions.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal", "transversally" refer to a direction generally perpendicular to the longitudinal direction.

An object of this disclosure is provide a simple and reliable medicament delivery device to perform an automatic calibration function.

According to an aspect of the present disclosure, the object is achieved by a reliable medicament delivery device according to claim 1.

There is hence provided a medicament delivery device, comprising: a housing having a proximal end and a distal end; a medicament container arranged within the housing and comprising a stopper and a delivery member; a biased delivery member cover associated with the housing and movable in relation to the housing; a biased plunger rod associated with the medicament container and movable in relation to the housing; a tubular rotator associated with both the delivery member cover and the biased plunger rod; and a cap assembly associated with the housing; wherein a gap is defined between the proximal end of the biased plunger rod and the stopper of the medicament container when the medicament delivery device is in an assembled state; and wherein the proximal end of the biased plunger rod is in contact with the stopper of the medicament container when the medicament delivery device is in a calibrated state.

According to one embodiment, the tubular rotator comprises a tubular body having at least one retaining member on its inner surface.

According to one embodiment, the tubular rotator comprises a tubular body having a first and a second retaining member on its inner surface According to one embodiment, the biased plunger rod comprises a counter retaining element configured to interact with the at least one retaining member or selectively with each of the first, the second and the third retaining members.

According to one embodiment, the tubular rotator comprises a tubular body having a retaining member on its inner surface; and the biased plunger rod comprises a first and a second counter retaining elements, wherein the first and the second counter retaining elements is configured to interact selectively with the retaining member.

According to one embodiment, the tubular rotator comprises a tubular body having a first, a second and a third retaining member on its inner surface; and the biased plunger rod comprises a counter retaining element, wherein the counter retaining element is configured to interact selectively with each of the first, the second and the third retaining members.

According to one embodiment, the retaining member is a radially inward protruding rib.

According to one embodiment, the first and the second retaining members are ledges.

According to one embodiment, the counter retaining member is a radially outward protruding arm.

According to one embodiment, the first and the second counter retaining members are grooves.

According to one embodiment, the medicament delivery device further comprises a medicament container configured to receive the medicament container.

According to one embodiment, the medicament container is axially fixed to the container carrier.

According to one embodiment, the container carrier comprises a dose stop arranged on its distal end.

According to one embodiment, the biased plunger rod further comprises an interaction member configured to interact with a counter interaction member on the distal end of the container carrier.

According to one embodiment, the interaction between the interaction member and the counter interaction member is configured to provide a feedback to a user of the medicament delivery device.

According to one embodiment, the biased delivery member cover comprises a guide element; and the tubular rotator comprises a tubular body arranged with a guide track on its outer surface; wherein the guide element is configured to interact with the guide track such that an axial movement of the biased delivery member cover causes the tubular rotator to rotate.

According to one embodiment, the biased delivery member cover comprises a delivery member cover link; wherein the guide element is arranged on the delivery member cover link.

According to one embodiment, the medicament delivery device is in the assembled state when the rotator is in a first rotation position which is defined when the biased plunger rod is in an initial position in which the counter retaining element is engaged with the first retaining member; when the biased delivery member cover is in a first retracted position in which the guide element is positioned on a first distal end point of the guide track; and when the biased delivery member cover is held in said position by the cap assembly which is releasably connected to the housing.

According to one embodiment, the medicament delivery device is in the assembled state when the rotator is in a first rotation position which is defined when the biased plunger rod is in an initial position in which the counter retaining element is engaged with the first retaining member; when the biased delivery member cover is in a first retracted position in which the guide element is positioned on a first distal end point of the guide track; and when the biased delivery member cover is held in said position by a knob assembly which axially fixed connected to the distal end of the housing.

According to one embodiment, the medicament delivery device is in the calibrated state when the rotator is in a second rotation position which is defined when the biased plunger rod is in a calibrated position in which the counter retaining element is engaged with the second retaining member, and when the biased delivery member cover is in a first extended position in which the guide element is positioned on a first proximal end point of the guide track after the cap assembly is removed from the housing.

According to one embodiment, the medicament delivery device is in the calibrated state when the rotator is in a second rotation position which is defined when the biased plunger rod is in a calibrated position in which the counter retaining element is engaged with the second retaining member, and when the biased delivery member cover is in a first extended position in which the guide element is positioned on a first proximal end point of the guide track after the knob assembly is turned from a first knob position to the second knob position.

According to one embodiment, the biased plunger rod is configured to move from the calibrated position to a final position in which the counter retaining element is engaged with the third retaining member, when the biased delivery member cover is moved from the first extended position to a second retracted position in which the guide element is positioned on a second distal end point of the guide track such that the medicament contained in the medicament container is thereby delivered to a user of the medicament delivery device.

According to one embodiment, the biased delivery member cover is axially movable from the first retracted position to the first extended position; from the first extended position to the second retracted position; and from the second retracted position to a second extended position in which the guide element is positioned on a second proximal end point of the guide track; such that the delivery member is extended from the delivery member cover when the delivery member cover is in the first and the second retracted positions; and is covered by the delivery member cover when the delivery member cover is in the first and the second extended positions.

According to one embodiment, the counter retaining element is configured to disengage with the second retaining member when the biased delivery member cover is axially movable from the first extended position to the second retracted position such that the rotator is moved from the second rotation position to a third rotation position.

According to one embodiment, the tubular rotator comprises a ramp surface arranged between the first and the second retaining member; wherein the counter retaining element is configured to move along the ramp surface from the first retaining member to the second retaining member.

According to one embodiment, the axial movement of the biased delivery member cover from the first retracted position to the first extended position causes the tubular rotator to rotate from the first rotation position to the second rotation position.

According to one embodiment, the medicament delivery device comprises a resilient member configured to proximally bias the biased delivery cover member.

According to one embodiment, the medicament delivery device can be an injection device, an on-body device, an inhalation device, a nasal sprayer or a medical sprayer.

According to one embodiment, the delivery member can be an injection needle, a catheter or a spray nozzle.

Other aspects, features, and advantages will be apparent from the summary above, as well as from the description that follows, including the figures and the claims.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The present application is directed to a feedback mechanism for a medicament delivery device and will now be described more fully hereinafter with reference to the accompanying drawings, in which exemplifying embodiments are shown. The feedback mechanism may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
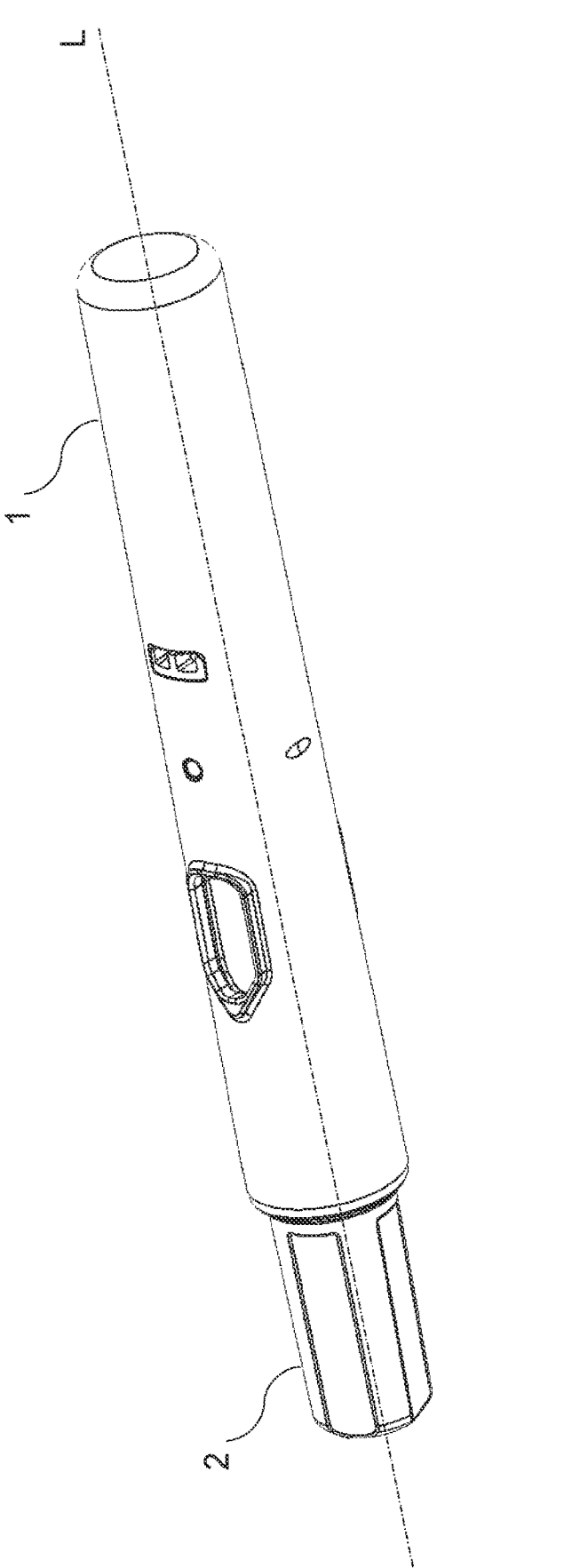
FIG. 1 displays a medicament delivery device of the first embodiment of the present disclosure.
Figure 2:
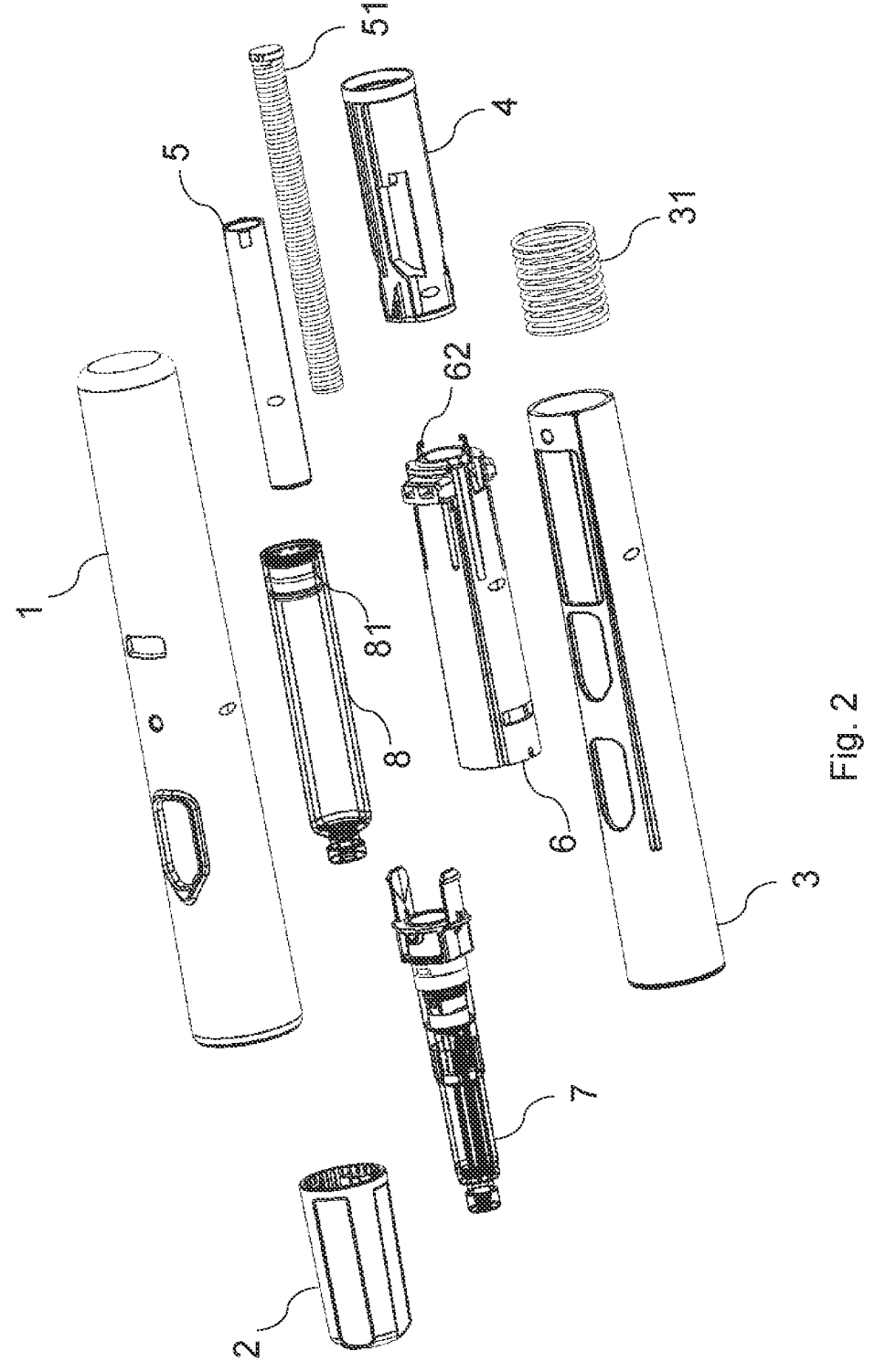
FIG. 2 displays an exploded view the medicament delivery device of FIG. 1 in detail.

FIG. 1 illustrates a medicament delivery device in the first embodiment of the present disclosure with a housing 1 having a proximal end and a distal end; and a cap assembly 2 arranged on the proximal end of the housing 1 in an assembled state of the medicament delivery device. As shown in FIG. 2, the medicament delivery device further comprises: a delivery member cover 3 axially movable but rotationally fixed in relation to the housing 1; a resilient member 31 arranged between the distal end of the delivery member cover 3 and an inner distal ledge of housing 1 and configured to bias the delivery member cover 3 in the proximal direction in relation to the housing 1; a tubular rotator 4, which is a tubular body arranged within the housing 1 and is rotatable but axially immovable in relation to the housing 1; a plunger rod 5 axially movably arranged within the housing 1; a drive element 51 arranged within the plunger rod 5 and configured to bias the plunger rod in the proximal direction; a container carrier 6 arranged within the housing 1, which is axially and rotationally fixed in relation to the housing 1 and configured to receive a medicament container 8. The medicament container 8 is configured to contain a medicament and comprises a stopper 81 arranged on its distal end and a pierceable membrane arranged on its proximal end. A delivery member assembly 7 comprises a delivery member configured to deliver a dose of medicament to the end user during a medicament delivery operation. The delivery member assembly further comprises: a delivery member hub configured to hold the delivery member; an inner cap configured to cover the delivery member; and a retainer configured to threadedly engage with the inner cap in the assembled state of the medicament delivery device. The cap assembly 2 is axially fixed to the inner cap of the delivery member assembly 7 and rotationally fixed with the inner cap in unidirectional rotation direction. The retainer is snap-fixed to the container carrier 6, such that the cap assembly 2 is attached to the housing 1 through the delivery member assembly 7 in the assembled state of the medicament delivery device. The cap assembly 2 can be detached from the housing 1 of the medicament delivery device when the cap assembly 2 and the inner cap have been both screwed and disengaged from the retainer. Such screwing movement turns into an axial movement of the delivery member hub due to a coupling between the inner cap and the delivery member hub whereby the delivery member is moved together with the delivery member hub towards the medicament container 8 establishing a fluid communication with the medicament container 8.

Figures 3, 4:
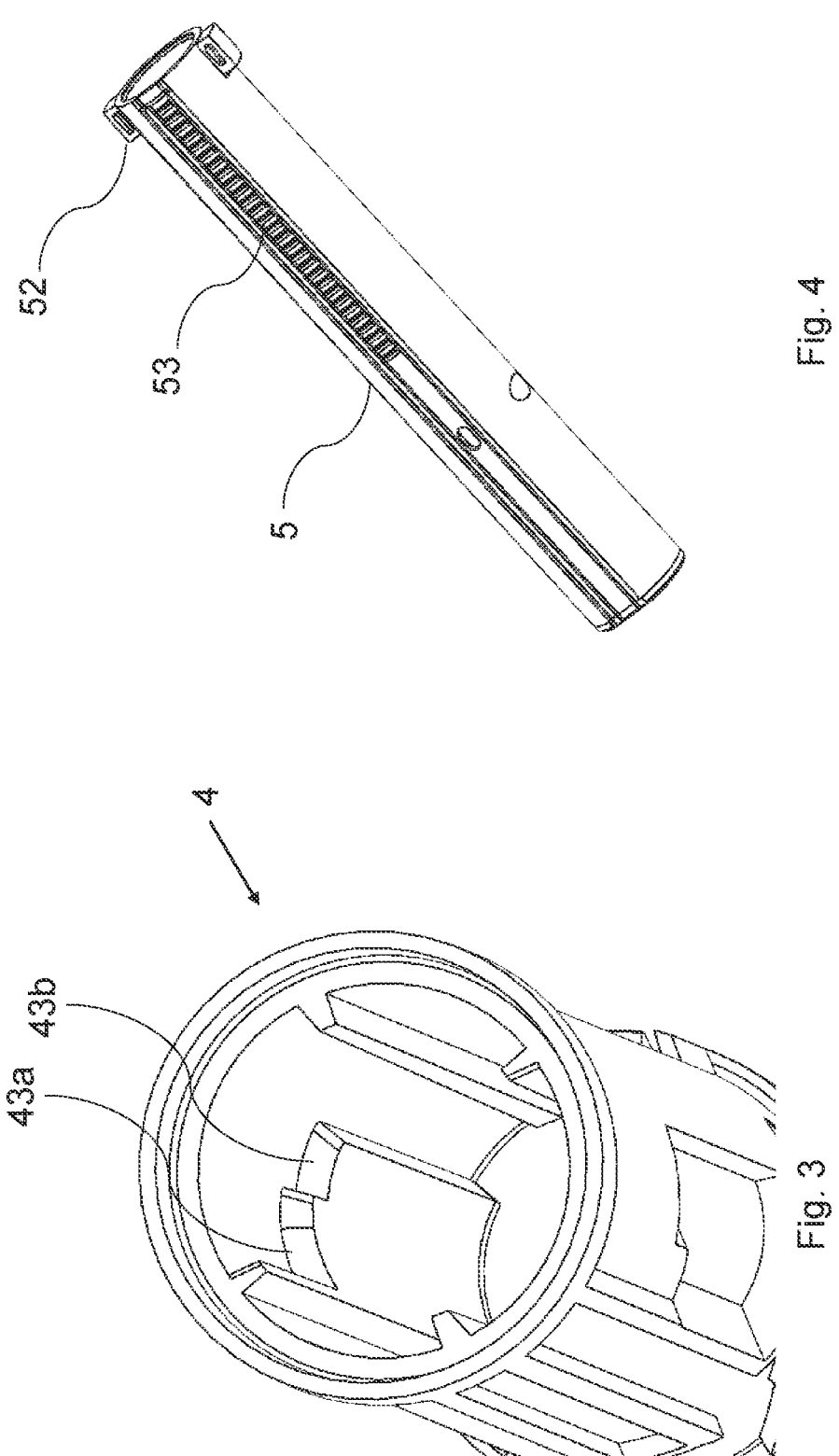
FIG. 3 displays a perspective view of a tubular rotator in the first embodiment.
FIG. 4 displays a perspective view of a plunger rod in the first embodiment.

FIG. 3 illustrates the tubular rotator comprising a first retaining member 43a and a second retaining member 43b arranged on the inner surface of the tubular body. The first and the second retaining member is configured to selectively engage with the counter retaining member 52 on the plunger rod 5 as shown in FIG. 4, such that the proximal axial movement of the plunger rod is prevented. The counter retaining member 52 is configured to rest on the first retaining member 43a when the tubular rotator 4 is in a first rotation position; and is configured to disengage from the first retaining member 43a and moves proximally under the biasing force of the drive element 51 to engage with the second retaining member 43b when the tubular rotator 4 is in a second rotation position.

Figures 7A, 7B:
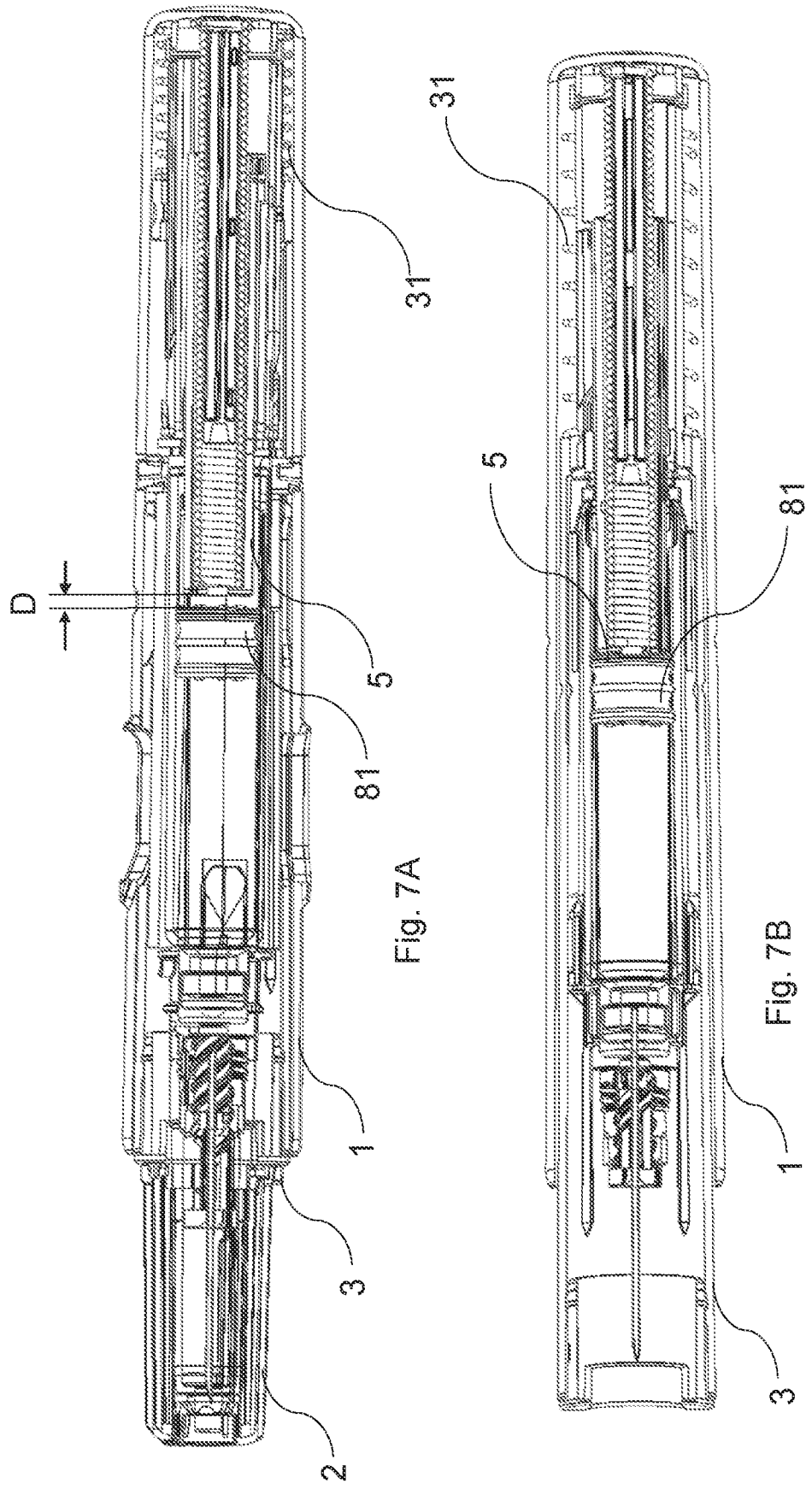
FIG. 7A-7B display cross section views of the medicament delivery device in an assembled state and in a calibrated state in the first embodiment.

The plunger rod 5 is in its initial position when the counter retaining member 52 is engaged with the first retaining member 43a. When the plunger rod is in its initial position, the medicament delivery device is in its assembled state wherein all components of the medicament delivery device have been assembled together and the device is ready to be delivered to an end user. As shown in FIG. 7A, when the medicament delivery device in the assembled state, there is a gap D defined by the proximal end of the plunger rod 5 and the distal end of the stopper 81 of the medicament container 8. Therefore, the risk of accidentally squeezing the stopper 81 forward during shipping the medicament delivery device and damage the sealing of the medicament container 8 by the plunger rod 5 can be prevented.

When the counter retaining member 52 of the plunger rod 5 is engaged with the second retaining member 43b of the tubular rotator 4, the plunger rod 5 is in a calibrated position, such that the medicament delivery device is also in its calibrated state. As shown in FIG. 7B, when the medicament delivery device is in its calibrated state, the proximal end of the plunger rod 5 is configured to be in contact with the stopper 81 of the medicament container 8, such that the gap D between the proximal end of the plunger rod 5 and the distal end of the stopper 81 is erased.

Figure 5:
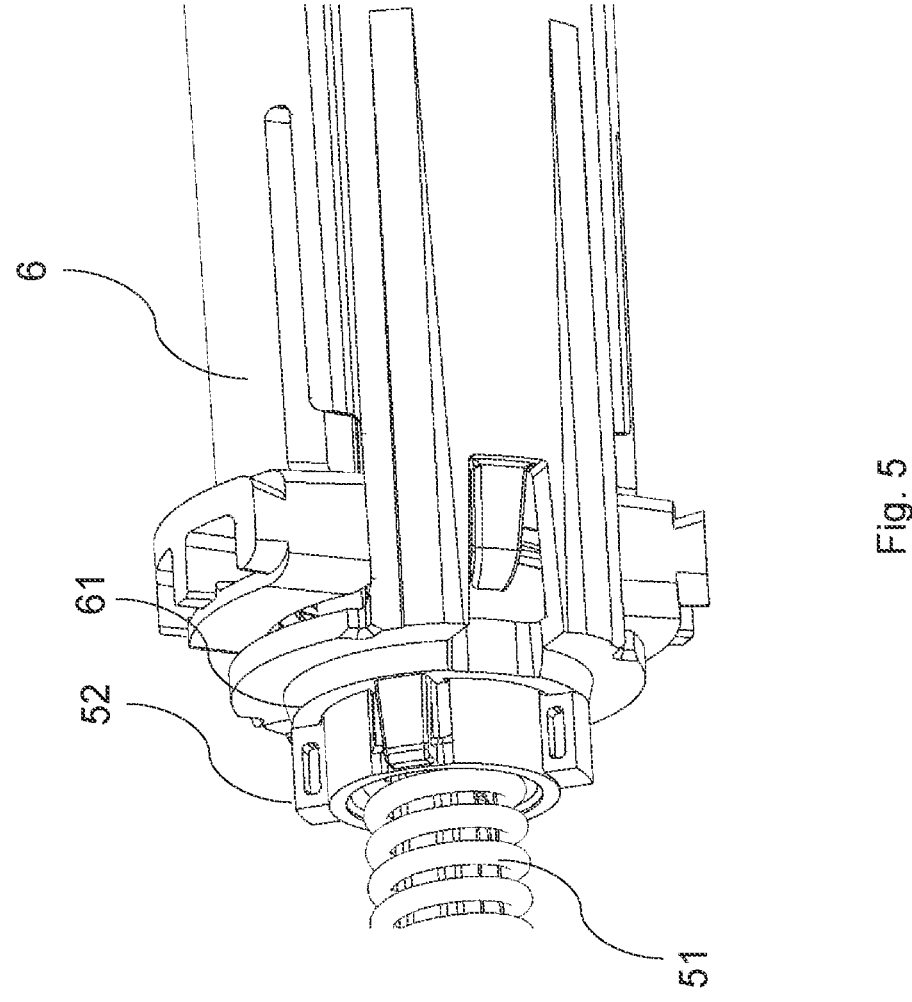
FIG. 5 displays a dose stop in the first embodiment.

When the medicament delivery device is in the calibrated state, a "zero dose" state is also defined, and the medicament delivery device is now ready to carry out the medicament delivery operation. The counter retaining member 52 of the plunger rod 5 is then configured to disengage from the second retaining member 43b of the tubular rotator 4 when the tubular rotator 4 is in a third rotation position, such that the plunger rod is moved proximally under the biasing force of the drive element 51 and actuates on the stopper 81 to deliver a dose of medicament. The medicament delivery operation is therefore started. The counter retaining member 52 of the plunger rod 5 is configured to be proximally moved in order to engage with a dose stop 61 when the plunger rod 5 is in a final position, such that the medicament delivery operation is ended. The dose stop 61 can be a ledge arranged on the distal end of the container carrier 6 as shown in FIG. 5 or a ledge arranged on an extra component or a third retaining member arranged on the inner surface of the tubular rotator 4. Such that the delivered dose is determined by the distance between the second retaining member 43b and the dose stop which is also the travel distance of the plunger rod 5 from the calibrated position to a final position.

The tubular rotator 4 is configured to interact with the delivery member cover 3. As shown in FIG. 6A, the delivery member cover 3 comprises a guide element 32 configured to move along a guide track 41 arranged on the outer surface of the tubular rotator 4. The interaction between the guide element 32 and the guide track 41 forces the tubular rotator 4 to rotate from the first to the second rotation position; and the second to the third rotation position.

Figure 6B:
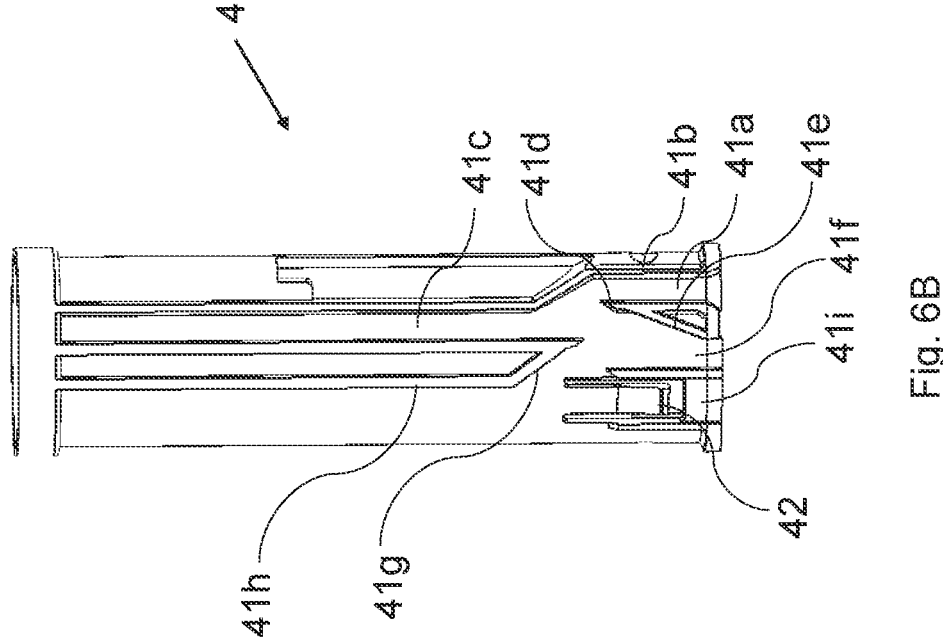
FIG. 6A-6B display a perspective and a side view of an outer arrangement of the tubular rotator and a guide element on a delivery member cover in the first embodiment.
Figure 6A:
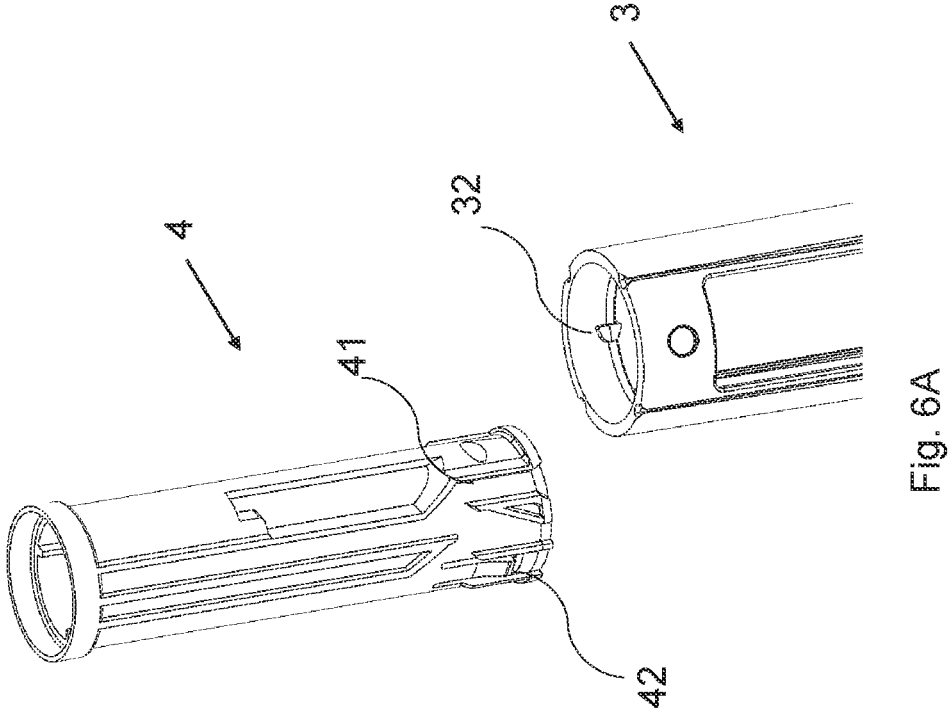

As shown in the FIG. 6B, during assembling, the tubular rotator 4 will be assembled into the housing 1; the delivery member cover 3 and the resilient member 31 will also be assembled into the housing 1; the guide element 32 will be positioned on a pre-assemble portion 41a of the guide track 41. Since the delivery member cover 3 is biased by the resilient member 31, the delivery member cover 3 will protrude from the proximal end of the housing 1. The last step of assembling is, placing the delivery member assembly 7 together with the cap assembly 2 towards the proximal end of the housing 1, pressing the proximal end of the delivery member cover 3 against the resilient member 31 and moving all the delivery member cover 3, the needle assembly 7 and the cap assembly 2 towards the distal end of the housing until the distal end of the needle assembly 7 attaches to the container carrier 6, such that the needle assembly 7 is bidirectional axially fixed with the container carrier 6. Such movement causes the guide element 32 to move along an assembling path 41b of the guide track 41, until the distal end of the needle assembly 7 attaches to the container carrier 6 and the needle assembly 7 together with the delivery member cover 3 no longer can move in the distal direction in relation to the housing 1. The delivery member cover 3 is then moved into a first retracted position and compress the resilient member 31 and the guide element 32 is thereby positioned on a first distal end point 41c. Since the needle assembly 7 is attached to the container carrier 6, the medicament delivery device is now properly assembled and is ready for delivering to the end user. When the medicament delivery device has been assembled, the cap assembly 2 is arranged on the proximal end of the housing 1, such that the proximal movement of the delivery member cover 3 is blocked by the cap assembly 2 as shown in FIG. 7A. The guide element 32 is then suspended on the first distal end point 41c of the guide track 41. Once the cap assembly 2 is detached and completely removed from the housing 1, the delivery member cover 3 is then moved to its first extended position under the biasing force of the resilient member 31, such that the proximal end of the delivery member cover is protruding from the proximal end of the housing 1 and configured to completely surround the delivery member as shown in FIG. 7B. When the delivery member cover 3 moves into the first extended position, the guide element 32 moves to the proximal end point 41f of the guide track 41; and passing the first inclined ledge 41d and the second inclined ledge 41e, such that the tubular rotator 4 is gradually rotated from the first rotation position to the second rotation position when the guide element 32 passes the first inclined ledge 41d and the second inclined ledge 41e.

The delivery member cover 3 can be manually pushed distally to its second retracted position for triggering the medicament delivery operation. When the delivery member cover 3 moves to the second retracted position, the guide element 32 is moved along a third inclined ledge 41g and an operation ledge 41h towards its second proximal distal end point of the guide track 41. When the guide element 32 passes the third inclined ledge 41*g* of the guide track 41, the tubular rotator 4 is rotated from the second rotation position to the third rotation position, such that the medicament delivery operation is started.

After the medicament delivery operation is ended, the delivery member cover 3 is no longer pushed to and retained on the second retraction position; the delivery member cover 3 is configured to move proximally to its second extended position under the biasing force of the resilient member 31 and configured to surround the delivery member again. The proximal movement of the delivery member cover 3 causes the guide element 32 proximally move along the operation ledge 41*h* of the guide track 41 to its second proximal end point 41*i* of the guide track 41. Before the guide element 32 moves into the second proximal end point 41*i* of the guide track 41, it passes a locking tongue 42 of the tubular rotator 4, such that the locking tongue 42 comprises a proximally directed cliff surface, therefore, once the guide element 32 moves into the second proximal end point 41*i* of the guide track 41, the further distal movement of the delivery member cover 3 is prevented due to the blocking between the guide element 32 and the proximally directed cliff surface of the locking tongue 42.

The delivery member protrudes from proximal end of the delivery member cover 3 when the delivery member cover 3 is in the first and the second retracted positions; and is covered by the delivery member cover 3 when the delivery member cover is in the first and the second extended positions.

The axial movement of the delivery member cover 3 driven by the resilient member 31 from the first retracted position to the first extended position causes the guide element 32 to move from the first distal end point 41*c* to the proximal end point 41*f* of the guide track 41. When the guide element 32 passes the first inclined ledge 41*d* and the second inclined ledge 41*e*, the tubular rotator 4 is gradually rotated from the first rotation position to the second rotation position.

It should be noted that, since the rotator 4 is engaged with the plunger rod 5 through the engagement between the first retaining member 43*a* and the counter retaining member 52, there will be a friction created between the first retaining member 43*a* and the counter retaining member 52 when the rotator 4 is rotating in relation to the plunger rod 5. The magnitude of the friction is depending on the accumulated force in the drive element 51, since it applies on the plunger rod 5, if the accumulated force in the drive element 51 is too high, the rotator 4 might not be rotated by the guide element 32 of the delivery member cover 3 which is proximally driven by the resilient member 31. Such a risk can be overcome by arranging a ramp surface to connect the first and the second retaining member. Therefore, the plunger rod 5 can move along the ramp surface from the first retaining member 43*a* to the second retaining member 43*b*. The rotation of the tubular rotator 4 from the first rotation position to the second rotation position is thereby mainly under the biasing force from the drive element 51.

The medicament delivery device in the first embodiment may further provide an audible/tactile feedback to the user of the medicament delivery device to indicate the progress of the medicament delivery operation. The feedback is provided by an interaction member 53 arranged on the plunger rod 5, preferably is a plurality ratchets; and a counter interaction member 62 arranged on the distal end of the container carrier 6. Once the plunger rod 5 proximally moves and passes the distal end of the container carrier 6, a continue feedback is thereby generated through the interaction between the interaction member 53 and the counter interaction member 62.

Figures 8A, 8B:
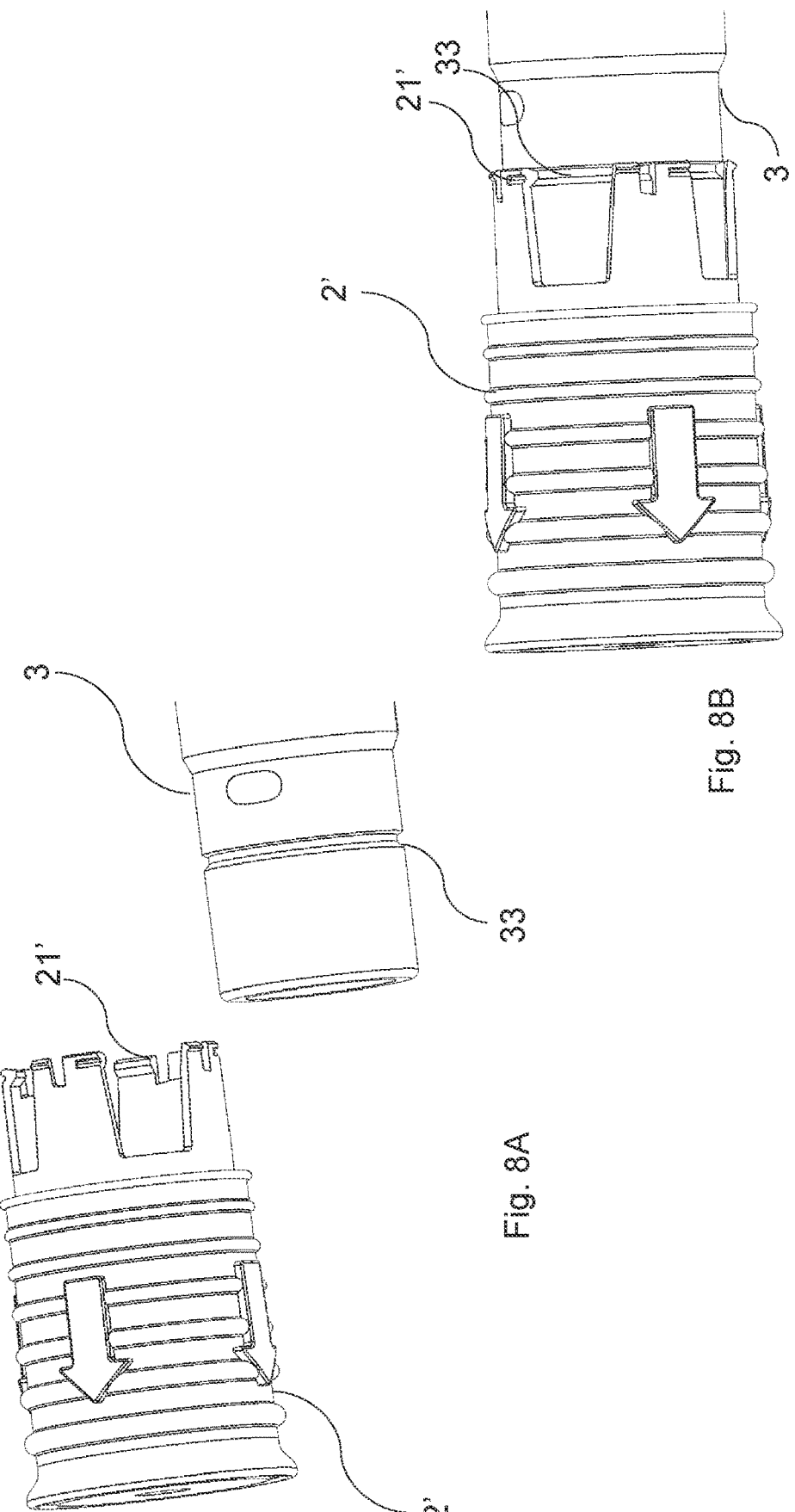
FIG. 8A-8B display perspective views of the arrangement of the cap assembly and the delivery member cover in the second embodiment of the present disclosure.

FIG. 8A-8B illustrate the second embodiment of the present disclosure. Most of arrangements in the second embodiment is same as described in the first embodiment. The delivery member is integral to the proximal end of the medicament container; the cap assembly 2' is arranged to be removed from the housing 1 by an axial pulling movement. The cap assembly 2' in the second embodiment comprises a gripping element 21' configured to grip on a groove 33 arranged on the proximal part of the delivery member cover 3. Once the medicament delivery device has been fully assembled, the gripping element 21' of the cap assembly 2 is arranged within the proximal end of the housing 1 and engages with the groove 33 of the delivery member cover, such that the inner surface of the proximal end of the housing 1 restricts the gripping element 21' of the cap assembly 2 from flexing radially outward. The cap assembly 2' is thereby attached to the housing 1 of the medicament delivery device through the engagement between the gripping element 21' and the groove 33 arranged on the proximal part of the delivery member cover 3. The gripping element 21' of the cap assembly 2 is prevented from flexing radially outward by being blocked by the inner surface of the proximal end of the housing 1 when the cap assembly 2' is pulled towards the proximal direction in relation to the housing, for removing the cap assembly 2' from the housing 1, such that the gripping element 21' will still grip on the groove 33 of the delivery member cover 3 and thereby the delivery member cover 3 is also proximally pulled together with the gripping element 21' and the cap assembly 2'. Such pulling movement will move the delivery member cover 3 from the first retracted position to the first extended position until the gripping element 21' of the cap assembly 2 has been completely moved out from the housing 1 and the gripping element 21' is able to disengage from the groove 33 of the delivery member cover 3 by flexing radially outward. The medicament delivery device is thereby moved from the assembled state to the calibrated state with the axial cap removal movement. Since the axial movement of the delivery member cover 3 from the first retracted position to the first extended position and to rotate the tubular rotator 4 from the first rotation position to the second rotation position, is mainly under the pulling force by the user of the medicament delivery device, the resilient member 31 is again no longer needed to accumulate a large force.

Figure 10:
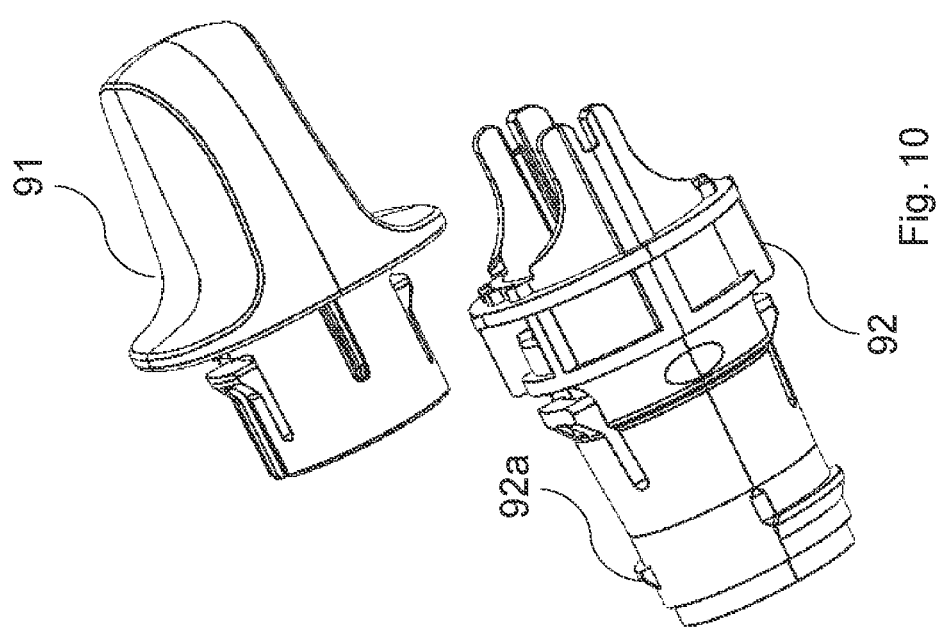
FIG. 9-10 display perspective views of a knob assembly in the third embodiment of the present disclosure.
Figure 9:
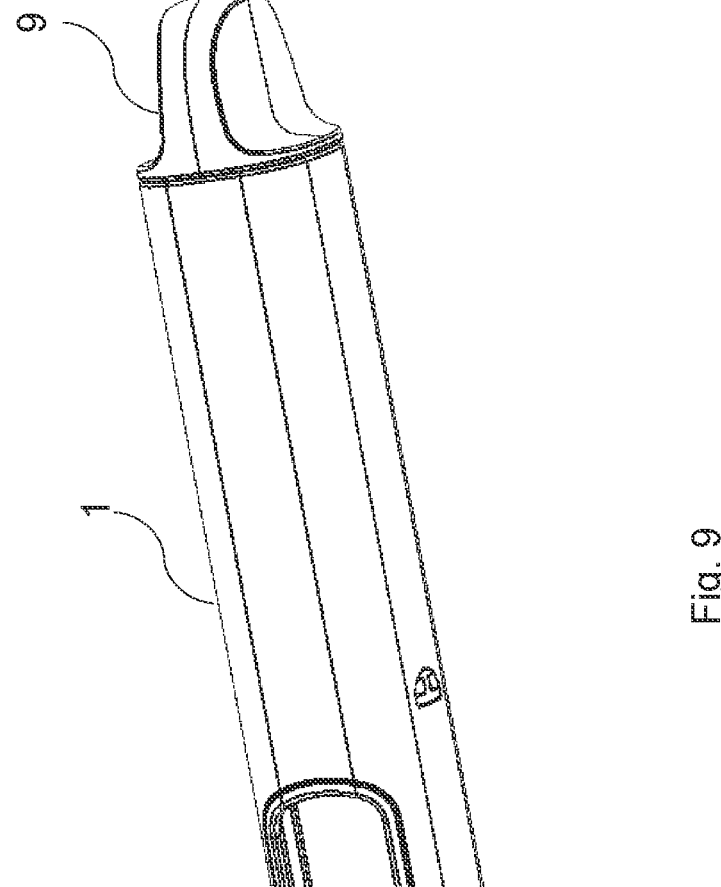
Figure 12:
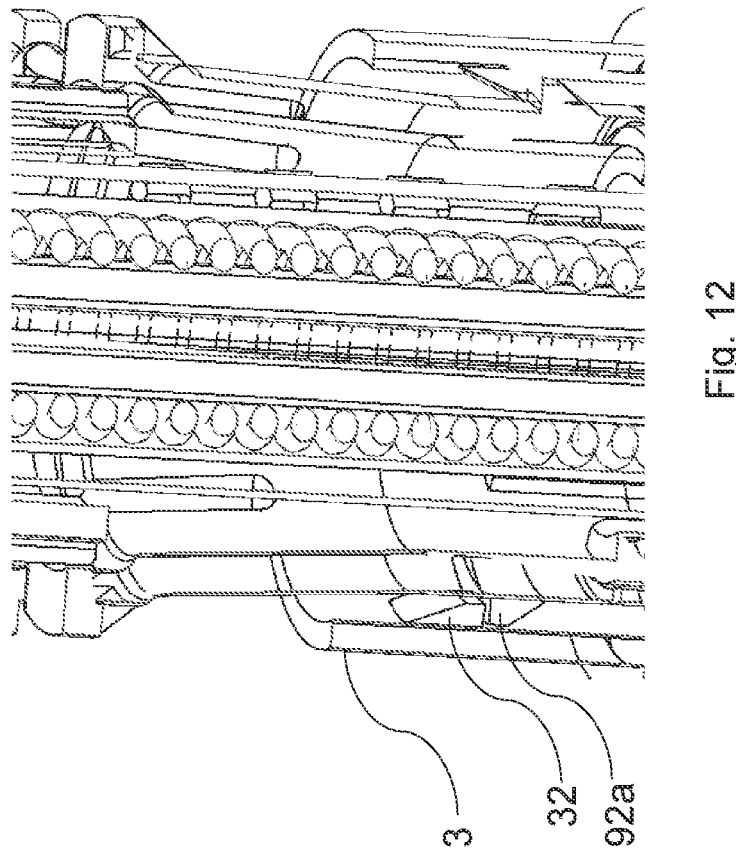
FIG. 12 displays a cross-section view of the interaction between the guide element and the knob assembly in the third embodiment.

FIG. 9 illustrates a third embodiment of the present disclosure. Most of arrangements in the third embodiment are the same as described in the first embodiment. The medicament delivery device in the third embodiment further comprises a rotatable knob assembly 9 arranged on the distal end of the housing 1. As shown in FIG. 10, the knob assembly 9 comprises a user accessible outer knob body 91 and an inner knob body 92. The distal end of the inner knob body 92 is received within the outer knob body 91 and the proximal end of the inner knob body 92 is received within the distal portion housing 1. The inner knob body 92 is axially and rotationally fixed to the outer knob body 91, such that the inner knob body 92 can be rotated together with the outer knob body 91 by the end user in relation to the housing 1. The knob assembly 9 is rotatable in relation to the housing 1 between a first knob position and a second knob position. As shown in FIG. 12, the inner knob body 92 comprises a holding member 92*a* configured to hold the guide element 32, so as the delivery member cover 3 is also hold by the holding member 92*a* in the first retracted position when the knob assembly 9 is in the first knob position. Such that the proximal movement of the delivery member cover 3 is prevented.

Figure 11:
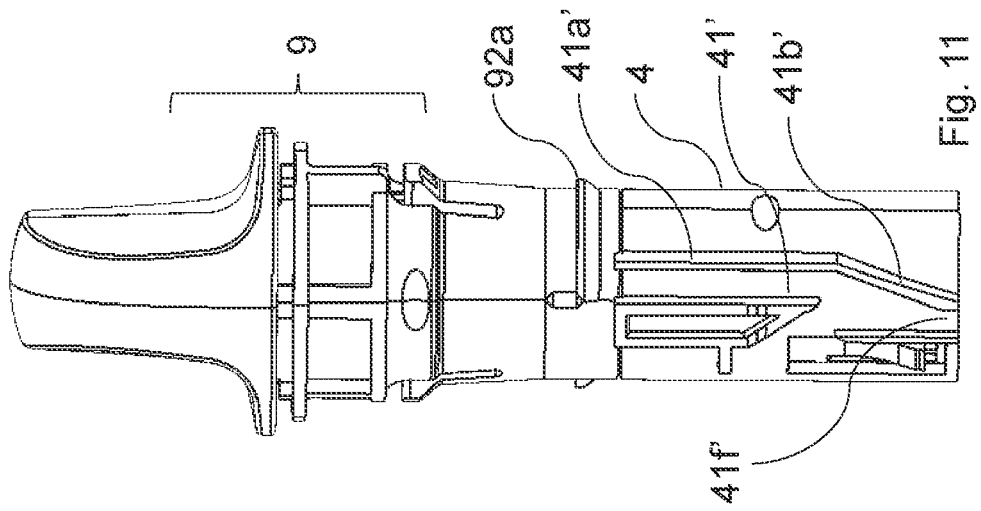
FIG. 11 displays a perspective view of the outer arrangement of the tubular rotator in the third embodiment.

As shown in FIG. 11, the guide track 41' of the tubular rotator 4 in the third embodiment comprises an initial guide ledge 41a' and a first inclined ledge 41b'. When the user of the medicament delivery device rotates the knob assembly 9 from the first knob position to the second knob position, the holding member 92a is misaligned with the guide element 32, such that the delivery member cover 3 is proximally moved under the biasing force of the resilient member 31. The guide element 32 therefore moves along the initial guide ledge 41a' and a first inclined ledge 41b' to the first proximal end point 41f of the guide track 41'. Once the guide element 32 passes the first inclined ledge 41b', the tubular rotator 4 is rotated from the first rotation position to the second rotation position.

Figure 14:
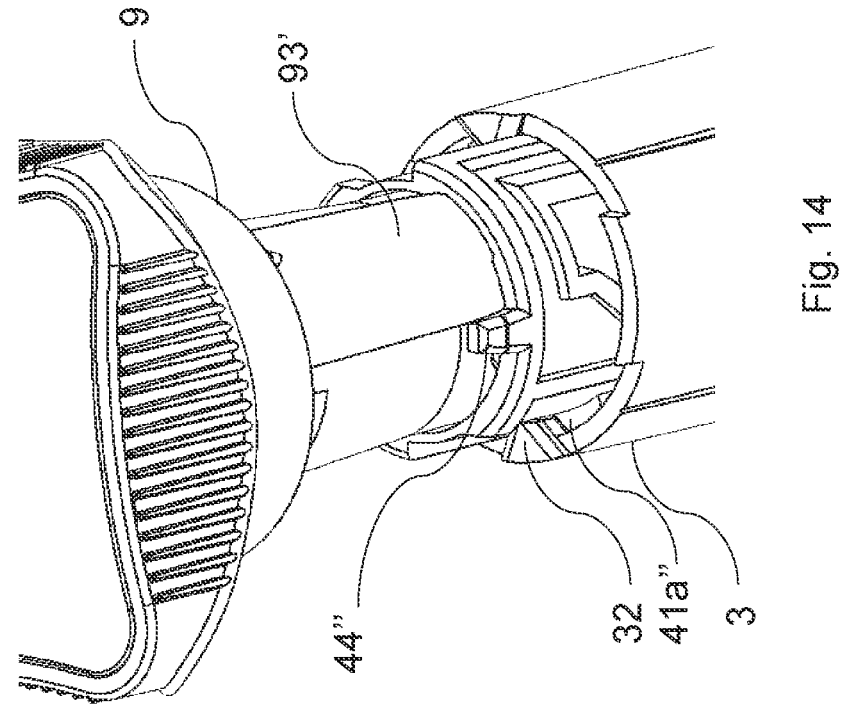
FIG. 14 displays a perspective view of the interaction between the guide element, the tubular rotator and the knob assembly in the fourth embodiment.
Figure 13:
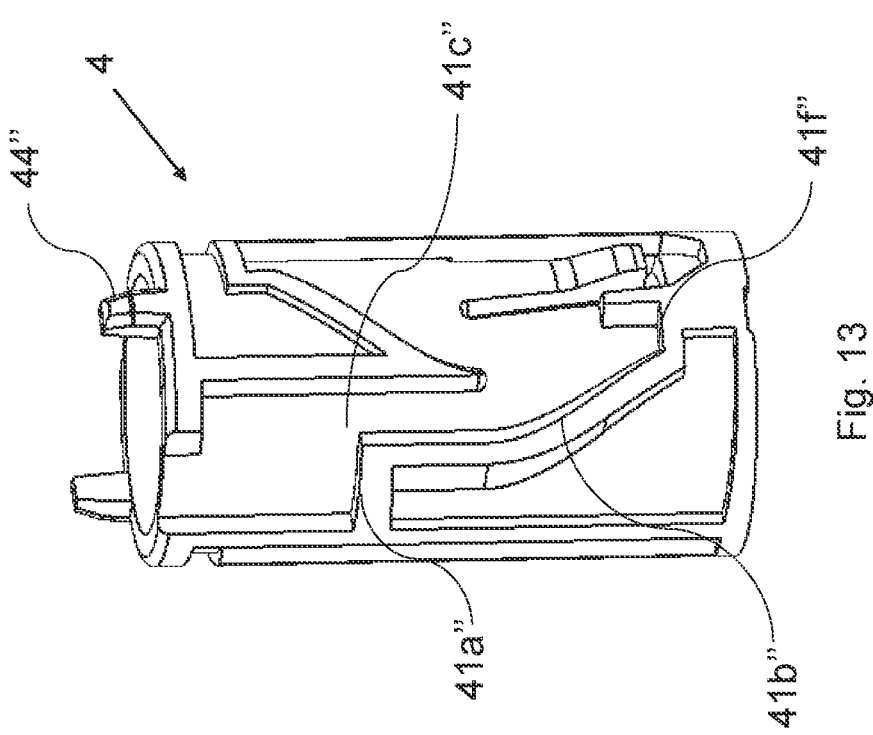
FIG. 13 displays a perspective view of the outer arrangement of the tubular rotator in the fourth embodiment of the present disclosure.

FIG. 13 illustrates a fourth embodiment of the present disclosure. Most of the arrangements in the fourth embodiment are the same as described in the third embodiment. The guide track 41" of the tubular rotator 4 in the fourth embodiment comprises an initial ledge 41a" configured to retaining the guide element 32 of the delivery member cover 3 in the first retracted position when the medicament delivery device has been properly assembled and is ready for delivering to the end user. The tubular rotator 4 in the fourth embodiment further comprises a turning portion 44", configured to engage with a turning pin 93' arranged on the knob assembly 9 as shown in FIG. 14. When the user of the medicament delivery device rotates the knob assembly 9, the turning pin 93' forces the tubular rotator 4 to rotate through the engagement with the turning portion 44". The rotation of the tubular rotator 4 release the guide element 32 from the assembled ledge 41a", and the delivery member cover 3 is therefore proximally moved to the first extended position under the biasing force of the resilient member 31. The guide element 32 is moved to its first distal end point 41c" of the guide track 41" and moved along a curve ledge 41b" of the guide track 41" with the proximal movement of the delivery member cover 3 towards the first proximal end point 41f of the guide track 41". Once the guide element 32 passes the curve ledge 41b", the tubular rotator 4 is rotated from the first rotation position to the second rotation position.

Figures 15A, 15B:
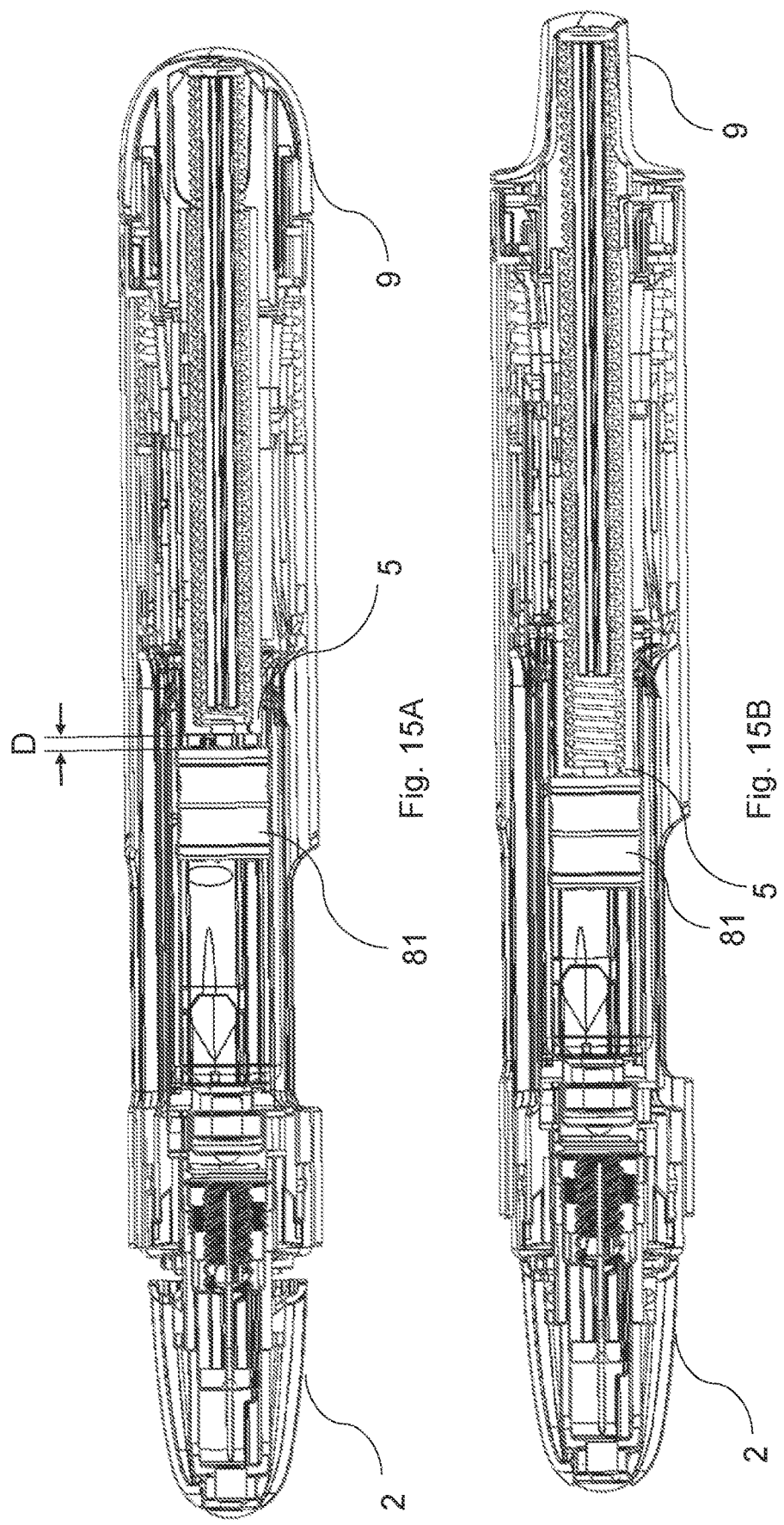
FIG. 15A-15B display cross-section views of the medicament delivery device in an assembled state and in a calibrated state in the third and the fourth embodiment.

FIG. 15A-15B illustrate the medicament delivery device in the assembled state and the calibrated state in the third and the fourth embodiments of the present disclosure. The turning movement of the knob assembly 9 from the first knob position, as shown in FIG. 15A to the second knob position, as shown in FIG. 15B turns the medicament delivery device from the assembled state to the calibrated state. In the third and the fourth embodiments the cap assembly 2 is no longer involved the auto calibration mechanism, so that the cap assembly 2 may be provided with more design flexibility.

Figure 17:
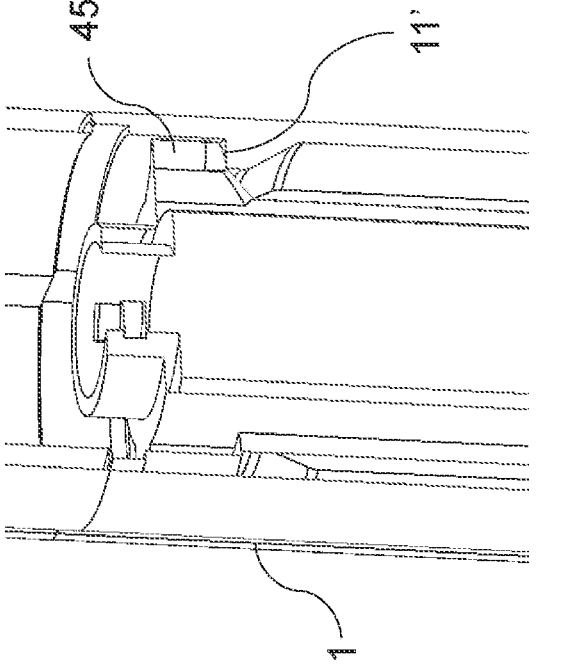
FIG. 16-17 display perspective views of a tubular rotator in an alternative embodiment of the present disclosure that the medicament delivery is arranged with auto penetration function.
Figure 17:
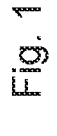
Figure 16:
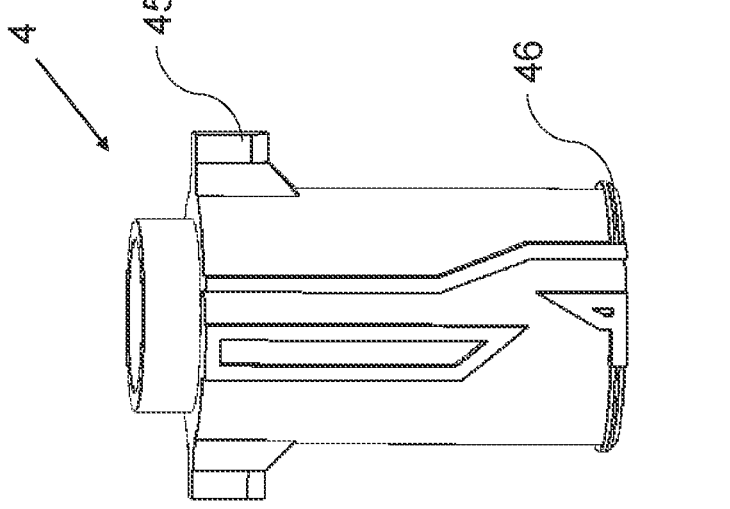

The auto calibration mechanism as described in the first to the fourth embodiment can also be used with a medicament delivery device with a movable medicament container, such as the medicament delivery device with auto penetration function. As shown in FIG. 16, the tubular rotator 4 for a medicament delivery device with auto penetration function may be modified with a holding arm 45 configured to engage with a holding shelf 11' arranged on the inner surface of the housing 1 when the medicament delivery device is in the assembled state and the calibrated state, as shown in FIG. 17. The tubular rotator may further comprises a connection portion 46 configured to snap on the distal end counter connection portion of the container carrier 6. So that once a delivery operation is triggered, the medicament delivery cover 3 turns the rotator from the second rotation position to the third rotation position with the way described above, the holding arm 45 will then be moved out from the engagement with the holding shelf 11'. The tubular rotator 4, the plunger rod 5, the container carrier 6, and medicament container 8 are thereby moved proximally under the biasing force of the drive element 51.

Figure 19:
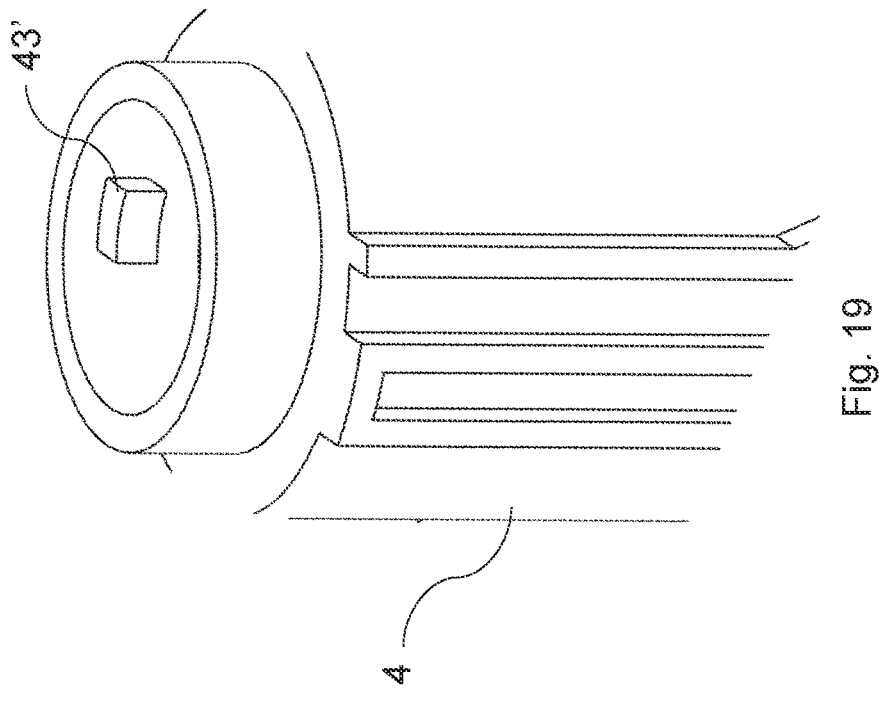
FIG. 18-19 display perspective views of a retaining arrangement between the tubular rotator and the plunger rod in an alternative embodiment of the present disclosure.
Figure 18:
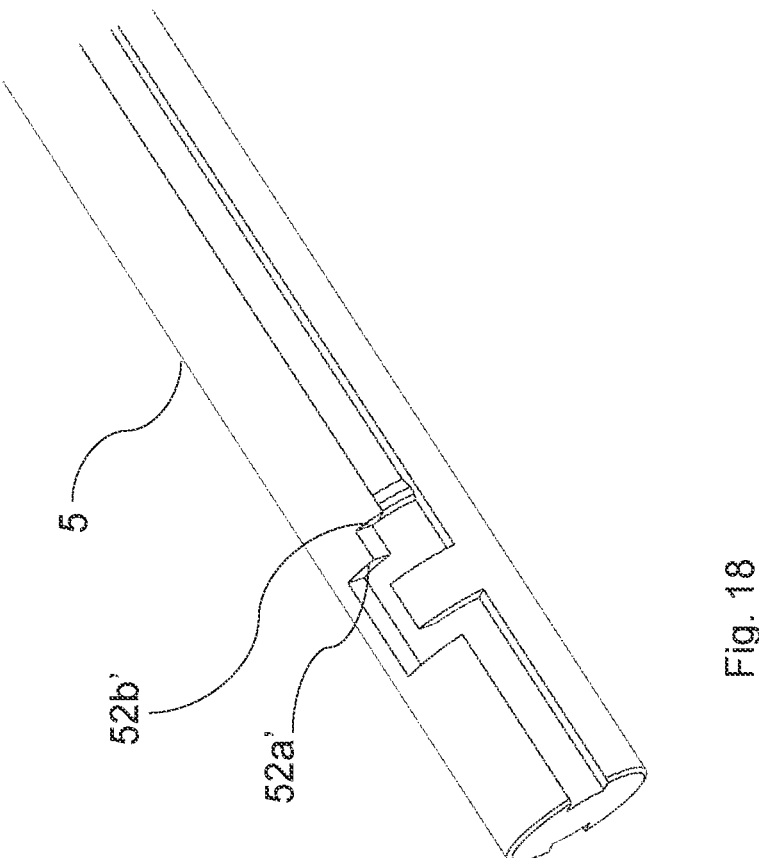

The arrangement of the retaining member of the tubular rotator 4 and the counter retaining member of the plunger rod 5 can also be arranged in opposite way for the auto calibration mechanism as described in the first to the fourth embodiment. As shown in FIG. 18, the counter retaining member of the plunger rod may be modified as the first counter retaining member 52a' and the second counter retaining member 52b'; the retaining member of the tubular rotator 4 can be modified as a retaining member 43' as shown in FIG. 19. The first counter retaining member 52a' is configured to engage with the retaining member 43' on the inner distal surface of the tubular rotator 4 when the tubular rotator 4 is in first rotation position. When the tubular rotator 4 moved into the second rotation position, the first counter retaining member 52a' is disengaged from the retaining member 43' and the plunger rod 5 moves proximally until the second counter retaining member 52b' engaged with the retaining member 43', such that the medicament delivery device is turned from the assembled state into the calibrated state.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A feedback assembly for a medicament delivery device comprising:

a container carrier having a longitudinal axis and comprising a flexible finger biased radially inward towards the longitudinal axis;

a plunger rod comprising an outer surface comprising a longitudinal feedback track and a protruding retaining member;

a resilient member engaged with the plunger rod that biases the plunger rod in a proximal direction;

where when the plunger rod is in an assembled state, the flexible finger is not engaged with the longitudinal feedback track and the plunger rod is axially fixed relative to the container carrier, and wherein when the resilient member pushes the plunger rod axially from a calibrated state to a final position, the plunger rod will move into and relative to the container carrier such that the flexible finger will engage the longitudinal feedback track to provide audible or tactile notification of medicament being expelled from a medicament container positioned with the container carrier.

2. The feedback assembly of claim 1, wherein the plunger rod is hollow and the resilient member is partially positioned inside the plunger rod and is engaged with a closed proximal end of the plunger rod.

3. The feedback assembly of claim 1, wherein the flexible finger located at a distal end of the container carrier.

4. The feedback assembly of claim 1, wherein the longitudinal feedback track is a plurality of ratchets.

5. The feedback assembly of claim 1 further comprising a tubular rotator surrounding the plunger rod and holds the plunger rod in a fixed axial position when the plunger rod is in the assembled state and in the calibrated state.

6. The feedback assembly of claim 5, wherein rotation of the tubular rotator relative to the plunger rod causes the plunger rod to move from the assembled state to the calibrated state.

7. The feedback assembly of claim 5, wherein rotation of the tubular rotator relative to the plunger rod causes the plunger rod to move from the calibrated state to the final position.

8. A medicament delivery device, comprising:

a housing having a longitudinal axis, a proximal end and a distal end;

a medicament container arranged within the housing and comprising a stopper and a delivery member;

a biased delivery member cover associated with the housing and movable in relation to the housing; and a feedback assembly comprising:

a container carrier holding the medicament container and comprising a flexible finger biased radially inward towards the longitudinal axis;

a plunger rod comprising an outer surface comprising a longitudinal feedback track and a protruding retaining member;

a resilient member engaged with the plunger rod that biases the plunger rod in a proximal direction;

wherein when the plunger rod is in an assembled state, the flexible finger is not engaged with the longitudinal feedback track and the plunger rod is axially fixed relative to the container carrier, and wherein when the resilient member pushes the plunger rod axially from a calibrated state to a final position, the plunger rod will move into and relative to the container carrier such that the flexible finger will engage the longitudinal feedback track to provide audible or tactile notification of medicament being expelled from the medicament container positioned with the container carrier.

9. The medicament delivery device of claim 8 further comprising a tubular rotator operatively associated with both the biased delivery member cover and the plunger rod.

10. The medicament delivery device of claim 9 further comprising a cap assembly operatively associated with the housing.

11. The medicament delivery device of claim 8, wherein a gap is defined between a proximal end of the plunger rod and the stopper of the medicament container when the medicament delivery device is in h assembled state, and wherein the proximal end of the plunger rod is in contact with the stopper of the medicament container when the medicament delivery device is in the calibrated state.

12. The medicament delivery device according to claim 10, wherein the tubular rotator comprises a first stop and a second stop on an inner surface that operatively engages the protruding retaining member on the plunger rod.

13. The medicament delivery device according to claim 12, wherein the biased delivery member cover comprises a guide element and the tubular rotator comprises a tubular body arranged with a guide track on an outer surface.

14. The medicament delivery device according to claim 13, wherein the guide element operatively interacts with the guide track such that an axial movement of the biased delivery member cover causes the tubular rotator to rotate.

15. The medicament delivery device according to claim 8, wherein distal and proximal movement of the biased delivery member cover causes the rotation of the tubular rotator relative to the plunger rod.

16. The medicament delivery device according to claim 13, wherein the medicament delivery device is in the assembled state when the tubular rotator is in a first rotation position which is defined when the plunger rod is in an initial position in which the protruding retaining member is engaged with the first stop and when the biased delivery member cover is in a first retracted position in which the guide element is positioned on a first distal end point of the guide track and when the biased delivery member cover is held in the first retracted position by the cap assembly which is releasably connected to the housing.

17. The medicament delivery device according to claim 16, wherein the medicament delivery device is in the calibrated state when the tubular rotator is in a second rotation position which is defined when the plunger rod is in a calibrated position in which the protruding retaining member is engaged with the second stop, and when the biased delivery member cover is in a first extended position in which the guide element is positioned on a first proximal end point of the guide track after the cap assembly is removed from the housing.

18. The medicament delivery device according to claim 14, wherein the axial movement of the biased delivery member cover from a first retracted position to a first extended position causes the tubular rotator to rotate from a first rotation position to a second rotation position.

19. The medicament delivery device according to claim 18, wherein the axial movement of the delivery member cover from the first extended position to a second retracted position causes the tubular rotator to rotate from the second rotation position to a third rotation position.

20. The medicament delivery device according to claim 12, wherein the tubular rotator comprises a ramp surface arranged between the first stop and the second stop such that the retaining member moves along the ramp surface from the first stop to the second stop.

* * * * *